United States Patent [19]

Takeda

[11] Patent Number: 5,222,020
[45] Date of Patent: Jun. 22, 1993

[54] ACQUISITION OF ARTERIAL RESPONSE PROCESS FOR PULSATING BLOOD FLOW AND ITS BLOOD PRESSURE MEASURING METHOD

[75] Inventor: Fumihide Takeda, Hiroshima, Japan

[73] Assignee: Takeda Engineering Consultant Inc., Hiroshima, Japan

[21] Appl. No.: 509,029

[22] Filed: Apr. 13, 1990

[30] Foreign Application Priority Data

Apr. 18, 1989 [JP] Japan .................................. 1-199870

[51] Int. Cl.⁵ ............................................. G06F 15/00
[52] U.S. Cl. ................................ 364/413.03; 128/672
[58] Field of Search ................ 364/413.03; 128/672, 128/677, 680, 681, 682

[56] References Cited

U.S. PATENT DOCUMENTS

| | | | |
|---|---|---|---|
| 4,301,512 | 11/1981 | Keith et al. ................ | 364/413.03 |
| 4,718,428 | 1/1988 | Russell .................... | 128/677 |
| 4,729,381 | 3/1988 | Harada et al. .............. | 364/413.03 |
| 4,735,213 | 4/1988 | Shirasaki .................. | 364/413.03 |
| 4,747,412 | 5/1988 | Yamaguchi ................ | 128/680 |
| 4,793,360 | 12/1988 | Miyawaki et al. .......... | 364/413.03 |
| 4,796,184 | 1/1989 | Bahr et al. ................ | 364/413.03 |
| 5,007,429 | 4/1991 | Treatch et al. ............. | 364/413.03 |

Primary Examiner—Roy N. Envall, Jr.
Assistant Examiner—Laura Brutman
Attorney, Agent, or Firm—Klarquist, Sparkman, Campbell, Leigh & Whinston

[57] ABSTRACT

Using a non-invasive blood pressure measuring apparatus that comprises a cuff, a pressurizing unit and bleeding valve, methods to acquire the arterial response to pulsating blood flow through an artery against the bleeding cuff's pressure are described. There are also described method for displaying in real time the entire arterial response on a display unit such as a CRT or LCD, which show the physical and psychological environment where a subject is placed. With the acquired data, accurate systolic and diastolic readings sensitive to environmental change are determined while monitoring in real time the entire arterial response. Remote monitoring of blood pressure can be done by transmitting the acquired data via telephone lines or directly to medical personnel or other instruments.

20 Claims, 4 Drawing Sheets

FIG. 5

ACQUISITION OF ARTERIAL RESPONSE PROCESS FOR PULSATING BLOOD FLOW AND ITS BLOOD PRESSURE MEASURING METHOD

TECHNICAL FIELD

In the field of non-invasive blood pressure measurement using a cuff, pressurizing unit and bleeding valves, this invention relates to a method of acquiring a response to the pulsating blood flow which produces stretching of the arterial wall against the bleeding cuff's pressure. The method includes displaying the cuff's fluctuating pressure on a display unit in terms of a variation in the height of the mercury column of a mercury manometer. The arterial wall stretching includes that which occurs before and after each systolic and diastolic pressure detection and between the two detections. The invention further relates to a method of measuring blood pressure by monitoring and recording the arterial response.

Apparatus according to the invention can display the simulated motion of a needle indicator of an aneroid manometer in addition to displaying the mercury column. Thus the invention does not require the manometers used previously in auscultatory methods. The invention can also graphically display in real time the arterial wall's subtle motion, which can not be detected by the auscultatory method with a stethoscope and a microphone. The wall motion is displayed in the form of time varying physical quantities such as acceleration, velocity and the like. This invention can therefore be used as the auscultatory method while monitoring the information being displayed.

BACKGROUND OF THE INVENTION

For acquiring the arterial response to the pulsating blood flow by non-invasive blood pressure measurement with a cuff, a pressurizing unit and bleeding valves, there have been the following available methods: displaying only the intensity level of the Korotkoff's sounds graphically by using a microphone, and displaying the cuff's oscillating pressure wave whose constant bleeding rate is filtered out.

However, there do not exist blood pressure measurement devices which display, in real time, information on the response to the pulsating blood flow and the bleeding of the cuff's pressure while simultaneously displaying the simulated mercury and aneroid manometers.

The invention resolves the following problems of prior measurement devices. Using current methods with a microphone, the acquired dynamic response of an artery to pulsating blood flow does not include information on arterial wall motion. That undetected motion includes movement that creates and annihilates the Korotkoff's sounds, movement immediately before and after the sounds, and movement not creating any Korotkoff's sounds.

The response to the pulsating blood flow which is obtained with the AC component of the cuff's pressure after filtering its DC component can show only the trend of the magnitude variation of the cuff's pressure oscillation. But the response can not show the dynamic expansion rate of the arterial wall. Furthermore, the arterial response to pulsating blood flow from which the systolic and the diastolic pressure are determined varies with the environment in which a subject is placed and the individual characteristics of the subject. Obtaining accurate systolic and diastolic readings for various subjects is difficult from judging only the trend of the magnitude of the cuff's pressure oscillation.

A method of acquiring the arterial response to pulsating blood flow is described in Japanese patent applications No. 61-118305 and No. 61-276785. The applications describe a filtering method. The method takes the first derivative of the cuff's pressure and then its integration with respect to time to obtain the increased amount of the cuff's pressure caused by the arterial expansion against the cuff's pressure. Thus it merely increases the accuracy of the filtering of the oscillating pressure. Since this integration is carried on with the first derivatives above a constant threshold value, it is easily affected by a small change in the bleeding rate.

Difficulty often arises in displaying the graphics of the dynamic parameters characterizing the expansion of the arterial wall, namely the displacement velocity of the wall and the parameters related to its acceleration change.

Therefore, with the bleeding rate nearly constant or even changing, this invention acquires the time trend of the artery wall's expansion caused by the pressure fluctuation in pulsating blood flow against the cuff pressure, acquires the wall motion that gives the accurate systolic and diastolic pressure, and monitors the arterial response to the pulsating blood flow.

Another difficulty in non-evasive blood pressure measurements is obtaining the regulated constant bleeding rate and monitoring the change in the bleeding rate over time. In subjects, the detection of Korotkoff's sounds in phases 1, 4 or 5 often becomes difficult, depending on the magnitude of the bleeding rate. Furthermore, the physical and psychological surroundings of a subject alter one's normal systolic and diastolic pressure readings significantly. In these cases, medical personnel using current auscultatory blood pressure measuring methods have difficulty in determining the cause for the changes.

Thus one object of the invention is to resolve the difficulties stated above by displaying in real time the bleeding of the cuff's pressure during the blood pressure measurements as well as displaying the simulated mercury manometer.

A further object of the invention is the measuring and monitoring of the arterial response in nearly real time for those subjects remote from clinics or hospitals.

SUMMARY OF THE INVENTION

To achieve these objects, the cuff's pressure is deflated at nearly a constant rate through a bleeding valve. With an artery pressed by the cuff's pressure, the pressure fluctuation of the pulsating blood flow stretches the arterial wall and in turn the wall's stretching fluctuates the cuff's pressure.

To obtain the acceleration component of the fluctuating cuff's pressure $P_c$, the second derivative of $P_c$ is taken over the time interval for which the acceleration of the bleeding rate becomes nearly zero, even when the bleeding rate is not constant. The second derivative is denoted $P_{sd}$. To acquire $P_{sd}$ without it being influenced by the bleeding rate, the quantity proportional to the expansion displacement of the artery when pressed as stated above is taken with a displacement transducer such as an optical sensor or the like. Its second derivative with respect to time is then denoted by $P_{sd}$. Also, the quantity proportional to the displacement velocity of the artery is taken with a velocity transducer such as an ultrasonic sensor or the like placed. It is denoted $P_{fd}$. The first derivative of $P_{fd}$ is then denoted by $P_{sd}$. Thus $P_{sd}$ may be obtained from two sources for verifying it value.

As for $P_c$, its mercury height's pressure in millimeters of mercury (mm Hg) is scaled on the Y-axis of a display and its time scale $T_c$ is given in seconds on the X-axis. As for the $P_{sd}$, its magnitude is enlarged on the Y-axis of $P_c$ and its time scale $T_{sd}$ is arbitrarily drawn on the Y-axis of $P_c$.

The region surrounded by $P_{sd}$ and time axis $T_{sd}$ is subdivided by each intersection of $P_{sd}$ and $T_{sd}$, namely T1, T2, ..., Tm-1, Tm, Tm+1, and so on. Among them, the integral over the positive region, i.e., its area, is taken as the increased value of the wall's displacement velocity GVinc, and the area of its negative region is taken as the decreased value of the displacement velocity GVdec. Their magnitudes are respectively denoted by the length on a bar graph, namely L0, L1, etc. for GVinc and D0, D1, etc. for GVdec and so on. Their scale is enlarged on the $P_c$'s Y-axis as that of $P_{sd}$. Tinc and Tdec are the time scale for the GVinc and GVdec, respectfully, and their unit is seconds.

The mean accelerating force GAinc for stretching the artery wall is defined as the division of each amplitude (L and S), which is the amount of increase in GVinc, by the time duration for expanding the wall. The mean accelerating force GAdec for contracting the wall is defined as the division of each amplitude (D), which is the amount of decrease in GVdec, by the time duration of contracting the wall. Thus the arterial response in terms of $P_c$, $P_{sd}$, GVinc, GVdec, GAinc and GAdec- may be graphically displayed.

The velocity component $P_{fd}$ may be obtained in a number of ways. It may be acquired by taking the first derivative of the cuff's pressure $P_c$ detected through a pressure transducer with acquiring $P_{sd}$ or it may be acquired directly through a transducer that detects the arterial wall motion.

Increases (L and S in GVinc) and decreases (D in GVdec) in the velocity component $P_{sd}$ of the arterial wall motion may be acquired by taking the difference between velocity components at each intersection (T1, ... Tm). For example, L1 is proportional to $P_{fd}(T2)$ minus $P_{fd}(T1)$ and D1 is proportional to $P_{fd}(T3)$ minus $P_{fd}(T2)$. Dividing L,S and D by the time spent producing the change produce the mean expanding and contracting acceleration forces GAinc and GAdec, respectively.

Another object of this invention is to provide a method of measuring blood pressure which gives nearly the same systolic and diastolic pressure readings as those obtained by the auscultatory method. For that purpose, when the amplitude of GVdec becomes consecutively larger than its threshold (two-thirds of its maximum amplitude Dmax), the cuff pressure giving the closest amplitude to that threshold is taken as the systolic pressure SYS. Similarly, when the amplitude of GVdec becomes consecutively smaller than its threshold, the cuff pressure giving the closest amplitude to the threshold is taken as the diastolic pressure DIA.

This invention also provides a method of measuring blood pressure which gives the accurate systolic and diastolic pressure readings by using the unique wave form of the acceleration component $P_{sd}$. The systolic pressure is transformed either into the change in time ▲Tm between Lm and Sm (where m=1,2,3) in the increased displacement velocity component GVinc on the wall, or their amplitudes' change ▲Am and so on. The cuff pressure is taken as the systolic reading SYS at the time the uniqueness is found for which either of ▲Tm and ▲Am or both start to increase. Furthermore, the mean value of the amplitudes D1 (at SYS), D0 (immediately before SYS) and D2 (immediately after SYS) is obtained. The cuff pressure at the time the decreased displacement velocity component GVdec on the wall becomes smaller than D1 is defined as the diastolic pressure reading DIA.

Another object of the invention is to provide a non-invasive blood pressure measuring apparatus comprising a cuff and tubes which can be wrapped around an artery in a finger, arm or a leg to be pressed; pressurizing and bleeding units for inflating the cuff and tubes; a pressure transducer for detecting the cuff's pressure; a displacement transducer for detecting displacement of the arterial wall motion; a velocity transducer for detecting a displacement velocity of the motion; a microcontroller for controlling each unit; a data processor and memory unit for carrying out the methods described; a display unit for showing the process data; and a data transmission unit.

With this apparatus, the fluctuating pressure reading acquired through the pressure transducer is displayed in real time as the height of a mercury column in the manometer glass tube. Then the cuff pressure on the subject's artery is raised a little above the systolic pressure before deflation. Setting the time axis at an arbitrary position, there are simultaneously displayed in real time the trend of the cuff's pressure $P_c$, the acceleration of the arterial wall's displacement $P_{sd}$, and the increased and decreased amount of GVinc and GVdec, and the time trend of GAinc, GAdec and $P_{fd}$.

There are also displayed Dmax, threshold Dmax - ⅔ being calculated with Dmax, and D1. Thus this apparatus measures the blood pressure non-invasively while monitoring the arterial response, and transmits the acquired data to other instruments through a network, a telemeter or the like.

The invention displays in real time the instantaneous velocity and acceleration of the arterial wall displacement which is obtained from fluctuations in the cuff's pressure. The invention also displays, in real time, the trend of the wall velocity change, and the characteristics of the time trend of the mean acceleration change.

The invention also displays in real time various wall expansion motions until the artery that is being pressed by the cuff's pressure relaxes to being free. Thus with the displayed arterial wall motion the invention acquires the following: the abnormal wall expansion of the arterial wall that can not be detected by the Korotkoff's sounds; the small abnormality accompanying a light irregular heart beat or the like; and the change in the arterial response due an unusual psychological and physical environment in which the subject is placed (for example under alert conditions, after exercising and under the alcoholic influence). In particular, the visualized displacement acceleration that is acquired by this invention is able to easily differentiate the noise created by non-arterial wall motion. The pressure reading acquired with the pressure transducer is converted to the height of the mercury column. It is displayed in real time inside the glass tube and is stored in memory. Thus even if this method is used along with an auscultatory method, it not only makes the detection of the Korotkoff's sounds in phases 1, 4 and 5 more certain, but also simplifies analyzing and storing the data in a way that can not be achieved by the blood pressure measurement techniques commonly practiced with mercury or aneroid manometers. Furthermore, transmission of the acquired data through a network or a telemeter is easily done.

The time changes of $P_{sd}$, GVinc, GVdec, GAinc and GAdec describe the expansion motion of the arterial wall. These changes may be used to non-invasively acquire information for the human cardiovascular system such as the degree of artery hardening and the like. Since apparatus according to the invention may also transmit the acquired data, measurements for subjects in remote locations can be monitored through a telephone hook-up. Medical personnel at the other end of the telephone line can instantaneously send appropriate instruction for treatment back to the subject through the apparatus.

If this apparatus is simultaneously used with an electrocardiograph, brain wave monitor or other instrument, the data obtained from these instruments can be displayed with the arterial response. Thus the apparatus not only increases the added value on such instruments, but also allows the data to be combined with other data.

$P_{sd}$ can alternatively be obtained by time-differentiation of the wall displacement and the displacement velocity acquired during non-invasive blood pressure measurement with optical and ultrasonic transducers respectively. Thus the invention works with blood pressure measuring methods that use displacement and displacement velocity transducers.

DETAILED DESCRIPTION

Figure 1:
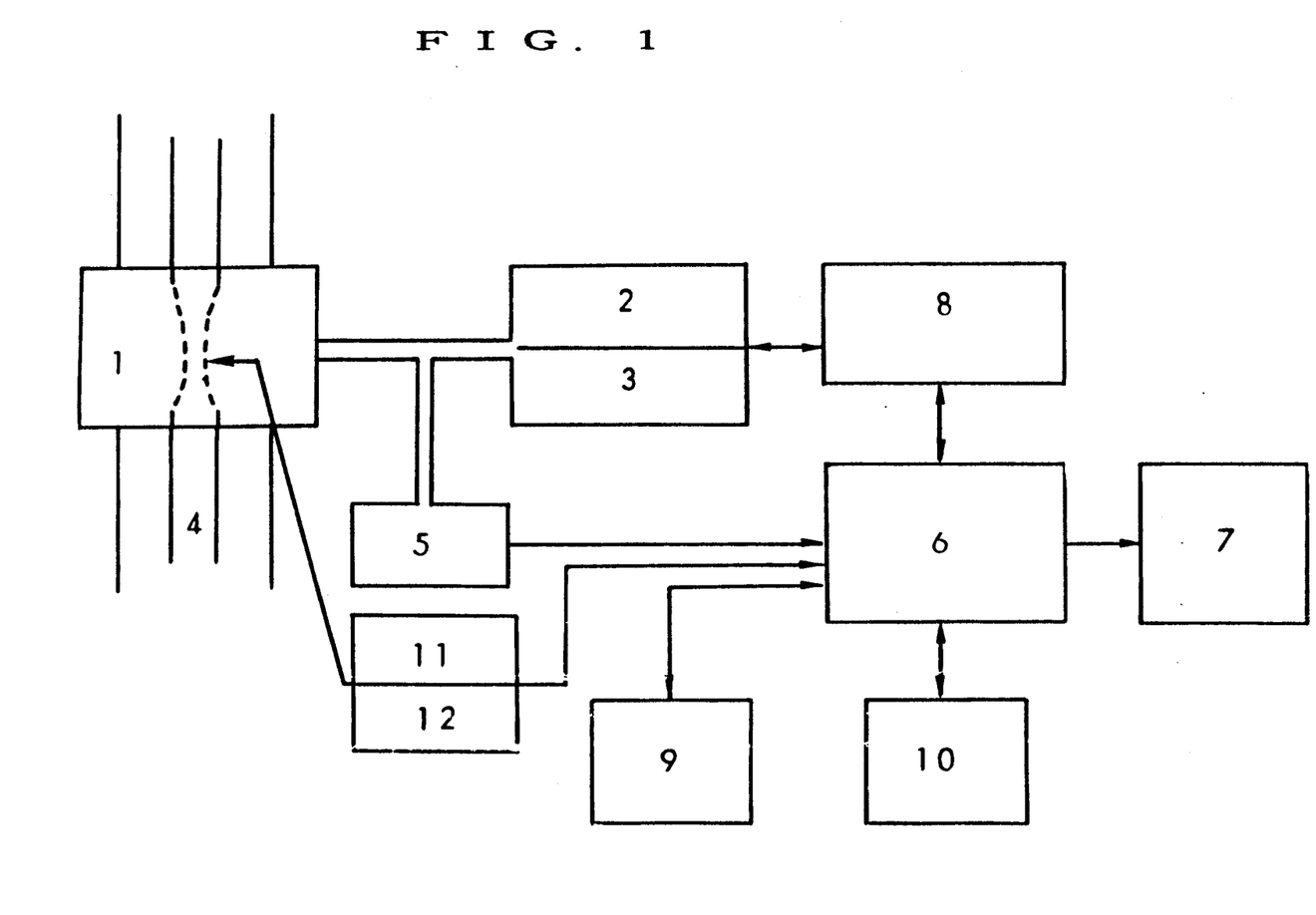
FIG. 1 is a block diagram of an apparatus according to the invention for making non-invasive blood pressure measurements.

Referring now to FIG. 1, there is shown a non-invasive blood pressure measuring apparatus according to the invention. The apparatus comprises a cuff 1 with embedded tubes which may be wrapped around an artery 4 within a finger, arm or leg. Connected to the cuff 1 are pressurizing and bleeding units 3 and 2 to inflate and deflate the tubes of cuff 1, respectively. A pressure transducer 5 is connected to the cuff for detecting the cuff's pressure as it is inflated and deflated and for communicating the pressure data as an electrical signal to a data processor 6. A displacement transducer 11 such as an optical sensor is connected to the cuff 1 for detecting the displacement of the arterial wall as it expands in response to the pulsating blood flow. A velocity transducer 12 such as a ultrasonic sensor is connected to the cuff 1 for detecting the velocity of the wall expansion. Transducers 11 and 12 communicate their respective data a electrical signals to the data processor 6.

The operation of the measuring apparatus is coordinated by a micro-controller 8 which controls the pressurizing unit 3, the bleeding unit 2 and the data processor 6. Data obtained from transducers 5, 11 and 12 and processed by data processor 6 may be stored in memory unit 9 and displayed on display unit 7. A data transmission unit 10 is also included in the apparatus. The unit 10 allows the acquired data to be transmitted to other instruments either directly or over the telephone lines and to receive data in return.

With the cuff inflated to a pressure $P_c$ by pressurizing unit 3, the artery 4 is squeezed by the cuff's pressure $P_c$. The pressure $P_c$ in the cuff is then deflated at nearly a constant bleeding rate through the bleeding valve unit 2. Against the artery 4, the pressure fluctuating of the pulsating blood flow starts to stretch the arterial wall which in turn moves to fluctuate the cuff's pressure.

Figure 2:
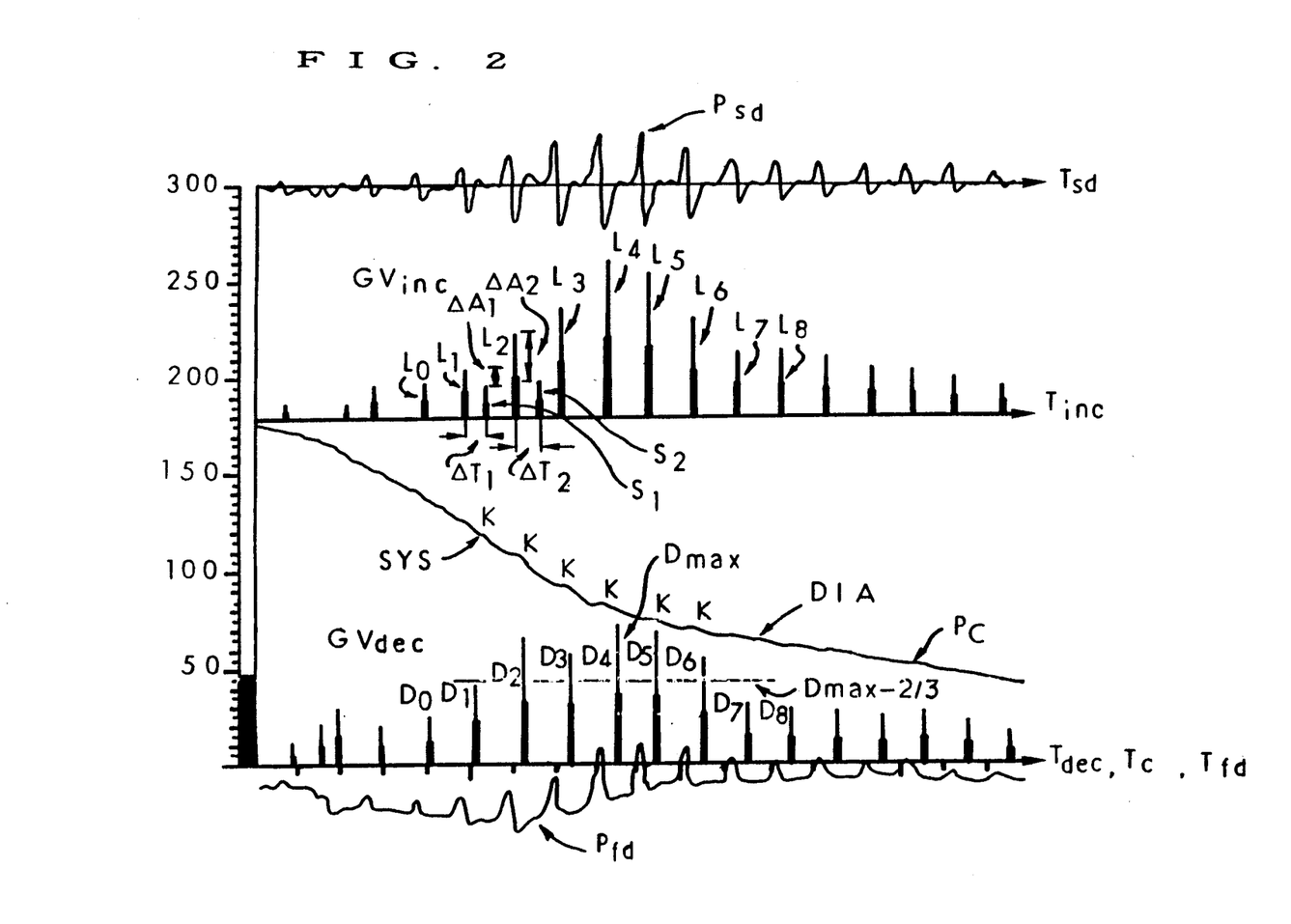
FIG. 2 is a display of the arterial response when the cuff's pressure's bleeding rate is fast and changing.

To obtain only the acceleration component of the fluctuating cuff's pressure $P_c$, the second derivative $P_{sd}$ of $P_c$ is taken at the data processing unit 6 over the time interval for which the acceleration of the bleeding rate becomes nearly zero. The relationship between $P_c$ and $P_{sd}$ is shown in FIG. 2 where the bleeding rate is not constant and in FIG. 3 where the bleeding rate is nearly a constant rate.

To acquire $P_{sd}$ without it being influenced by the bleeding rate, the quantity proportional to the wall's displacement of artery 4 pressed as stated above is taken with displacement transducer 11. Its second derivative with respect to time is denoted by $P_{sd}$. Also, the quantity proportional to the wall's displacement velocity of artery 4 is directly taken with velocity transducer 12 placed on the cuff. It is denoted by $P_{fd}$. The first derivative of $P_{fd}$ is $P_{sd}$. The numerical values processed at the data processing unit 6 are displayed on the displaying unit 7.

To display $P_c$, the pressure is simulated as the mercury height in mmHg at the display unit 7 with the Y-axis being pressure in mmHg and the X-axis being its time scale Tc in seconds. To display $P_{sd}$, its magnitude is enlarged on the Y-axis and its time scale $T_{sd}$ is arbitrary drawn at 300 on the Y-axis. The pressure fluctuation of Pc due to the pulsating blood flow is enlarged on $P_{sd}$ without being influenced by the bleeding rate where the subjects in FIGS. 2 and 3 are different.

Figure 3:
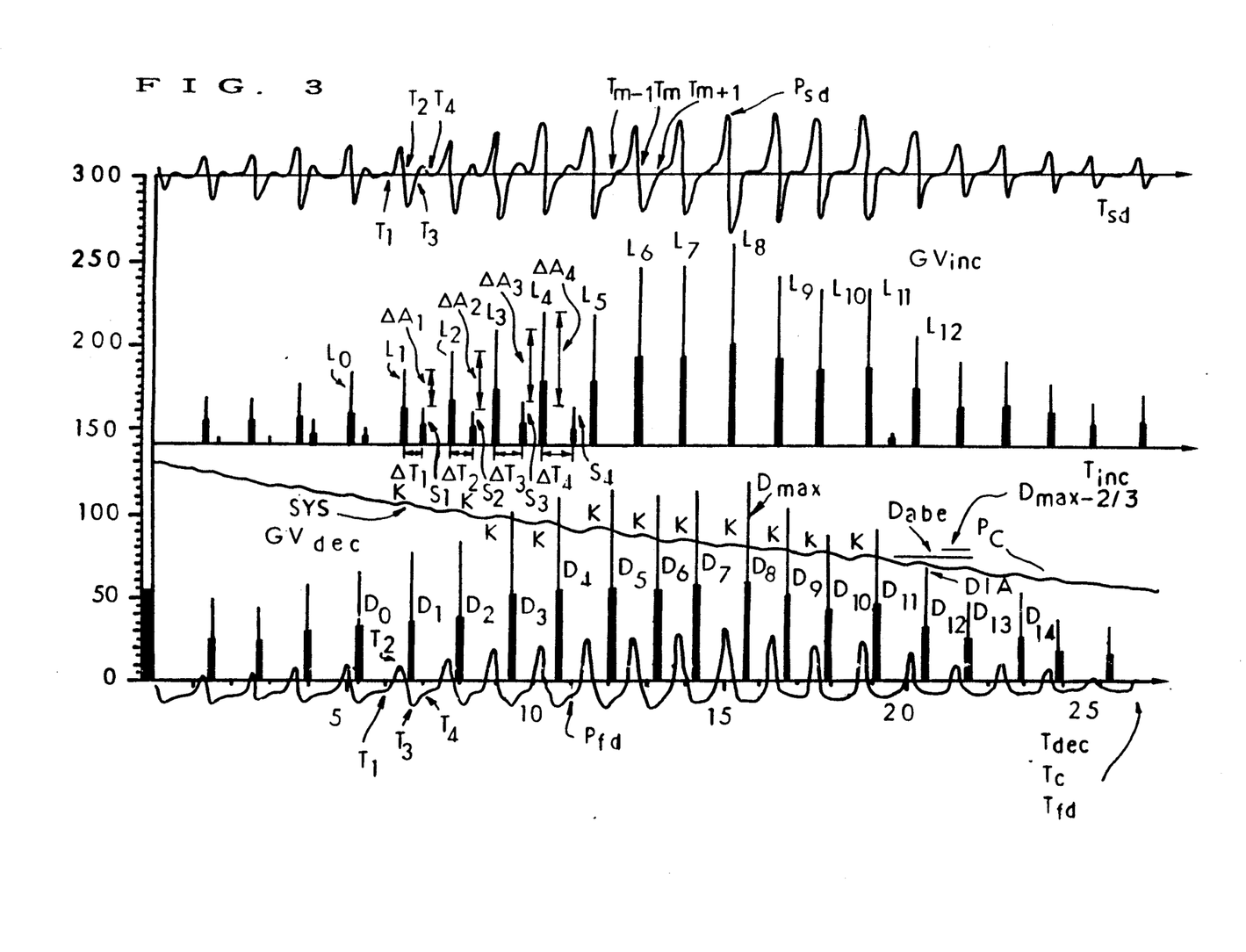
FIG. 3 is a display of the arterial response when the bleeding rate is nearly a specified constant.

Next, as shown in FIG. 3, the region surrounded by $P_{sd}$ and time axis $T_{sd}$ is subdivided by the every intersection of $P_{sd}$ and $T_{sd}$, namely T1, T2 . . . , Tm-1, Tm, Tm+1 and so on. Among them the integral over the positive region, i.e., its area, is taken as the increased value of the wall's displacement velocity Gvinc, and the area of its negative region is taken as the decreased value of the displacement velocity GVdec. Their magnitudes are respectively denoted by the length on the bar graph, namely L0, L1, and D0, D1, and so on. Their scale is enlarged on the Y-axis. Tinc and Tdec are the time scales for GVinc and GVdec, respectively, and their unit is seconds.

The means accelerating force of the expansion acting on the artery wall, GAinc, is calculated at the data processing unit 6 by dividing GVinc by the time interval for expanding the wall. The mean contracting force GAdec is calculated at unit 6 by dividing GVdec by the time interval for contracting the wall. Their magnitudes and time scales can be shown in real time on the Y and the X-axis at the display unit 7 in a monitor similar to showing GVinc and GVdec.

According to the process for acquiring the arterial response described in this first example, the pressure fluctuation of the pulsating blood flow is effectively obtained and shown in FIGS. 2 and 3 as $P_{sd}$ along with its time trend, which is proportional to the instantaneous acceleration stretching the arterial wall.

From the instantaneous acceleration on the arterial wall motion, the change of the displacement velocity induced by the wall's stretching is calculated as the integration over the positive region of instantaneous acceleration $P_{sd}$ with respect to time. Its magnitude is shown in GVinc in FIGS. 2 and 3. The quantity corresponding to the velocity change due to the wall contraction is calculated as the integration over the negative region of instantaneous acceleration $P_{sd}$ with respect to time. Its magnitude is shown as GVdec in FIGS. 2 and 3. The quantity proportional to the average displacement acceleration acting on the wall motion is taken as GAinc and GAdec and is calculated by dividing GVinc and GVdec by the corresponding time interval for the integrations respectively. Thus these methods effectively acquire the non-invasive arterial response process.

Next a second example of acquiring the arterial response using the apparatus shown in FIG. 1 is described. This method is to obtain the increments of the wall's displacement velocity at the data processing unit in the following way. The displacement velocity of the wall, $P_{fd}$, taken as the first derivative of Pc with respect to time is shown in the lower section of FIG. 3 along with acceleration $P_{sd}$ taken as the second order time derivative of Pc. The time scale of either this $P_{fd}$ or other $P_{fds}$ obtained by other methods and $T_{sd}$, namely T1, ..., Tm, and so on, the corresponding velocity components, i.e., $P_{fd}(T1)$, ..., and $P_{fd}(Tm)$, are obtained. The increased or the decreased amount on the displacement velocity of the arterial wall motion, i.e., GVinc and GVdec, are obtained by the difference between the two of these. For example, L1 and D1 are proportional to $P_{fd}(T2) - P_{fd}(T1)$ and $P_{fd}(T3) - P_{fd}(T2)$ respectively. Furthermore, S1 is proportional to $P_{fd}(T4) - P_{fd}(T3)$. Thus Gvinc and GVdec are divided by the corresponding time intervals and they are matched with the mean expanding and contracting accelerations GAinc and GAdec respectively.

According to the acquired arterial response process in this second example, the pressure fluctuation of the pulsating blood flow is proportional to the instantaneous displacement velocity of the arterial wall, which is shown as $P_{fd}$ in FIGS. 2 and 3 along with its time trend. With this instantaneous velocity change on the arterial wall motion, the same GVinc and GVdec as in the first example are calculated as the changes of the displacement velocity for each stretching process. Furthermore, the mean displacement acceleration of the wall motion, as in the first example, is GAinc and GAdec, which are calculated by dividing GVinc and GVdec by each time interval respectively. Thus this method effectively acquires the non-invasive arterial response process.

A third example is to be explained. This uses the arterial response acquired by the above method in order to obtain a blood pressure measurement which gives nearly the same systolic and diastolic pressure readings as the auscultatory method. In this non-invasive blood pressure measurement, the following data analysis is made at unit 6. As shown in FIG. 3, when the amplitude of GVdec becomes consecutively larger than threshold Dmax-⅔ (being two-thirds of the maximum amplitude Dmax), the cuff pressure giving the closest amplitude to that threshold is taken a the pressure reading of the wave crest in the pulsating blood flow, namely systolic pressure SYS. Similarly, when the amplitude of GVdec becomes consecutively smaller than the threshold, the cuff pressure giving its first smaller amplitude is taken as the pressure reading of the wave trough in the pulsating blood flow, namely diastolic pressure reading DIA.

According to this non-invasive blood pressure measurement method as shown in FIGS. 2 and 3, if threshold Dmax-⅔ is obtained as being two-thirds of the maximum amplitude Dmax, there are seen the GVdec's amplitudes, D1, D2, D3 and etc., getting consecutively larger than the threshold. Then the cuff's pressure reading at the time when the amplitude becomes the closest to that threshold is 120 mmHg and 101 mmHg for the cases in FIGS. 2 and 3 respectively. They are the wave crest values of the pulsating blood flow, namely the systolic pressure readings. When D7 and D8 are detected at which GVdec consecutively gets smaller than Dmax-⅔, the cuff pressure 65 mmHg which gave amplitude D7 the first smaller amplitude is the wave trough of the pulsating blood flow, namely the diastolic pressure reading. Similarly, when D12, D13 and D14 are detected at which GVdec consecutively gets smaller than Dmax-⅔, the cuff pressure 67 mmHg which gave amplitude D12 the first smaller amplitude is the wave trough of the pulsating blood flow, namely the diastolic pressure reading.

This measuring method shows that since every Korotkoff's sound simultaneously taken with a stethoscope during the measurement (labeled as k on the Pc curves in FIGS. 2 and 3), including the sound of phase 1 defining the systolic pressure reading, agrees with the pulsating process characterized with L1 and D1 in FIGS. 2 and 3. The method also shows that the annihilation of the Korotkoff's sound of phase 5 similarly agrees with the arterial wall expansion process characterized with L7 and D7 in FIG. 2, and with L12 and D12 in FIG. 3. Thus this method is also effective as well.

Next, a fourth example is to be explained. This example is for the blood pressure measurement method giving the accurate systolic and diastolic readings by using the unique characteristics on the arterial response acquired through the method described in examples 2 and 3. The data analysis is also made at unit 6 in the following way. As shown in FIGS. 2 and 3, the unique wave form in the neighborhood of the wall's displacement acceleration $P_{sd}$ on the artery wall motion to determine the systolic pressure reading is transformed into either the changes of the time difference ▲Tm between Lm and Sm in the increased displacement velocity component GVinc on the wall or their amplitudes' change ▲Am where m=1,2,3, and so on. The cuff pressure is taken as the systolic reading SYS at the time the uniqueness is found for which either of the ▲Tm and the ▲Am or the both start to increase consecutively as shown in FIGS. 2 and 3. Furthermore, the mean value of the amplitudes D1 (at SYS), D0 (at right before SYS) and D2 (at right after SYS) which is indicated as Dave in FIG. 3 is obtained. The cuff pressure at the time the decreased displacement velocity component GVdec on the wall becomes consecutively smaller than either D1 or Dave is defined as the diastolic pressure reading DIA.

According to the measuring method, the unique patterns in the neighborhood of $P_{sd}$ giving the systolic pressure are obtained, as shown in FIGS. 2 and 3. They are the continuous increase as in ▲T1, ▲T2, ▲T3 and ▲T4 which are the time difference between the pairs L1 and S1, L2 and S2, L3 and S3, and L4 and S4 on GVinc; and the continuous increase of amplitude L as in A1, A2, A3 and A4. Therefore, the arterial wall stretching giving the systolic pressure shows agreement with the pulsating process characterized with L1 and D1. The systolic pressure readings are then 120 mmHg and 101 mmHg for FIGS. 2 and 3 respectively. They agree with those in the auscultatory method stated above.

Furthermore, the arithmetic average of amplitudes D1, D0 (right before) and D2 (right after) is calculated as Dave. During the course on which D12, D13 and D14 are consecutively getting smaller than either of the D1 and Dave, the cuff's pressure which gives amplitude D12 the first smaller amplitude is the diastolic pressure reading 69 mmHg which is the same as that given by the auscultatory method. as for FIG. 2, since Dave is nearly the same as Dmax-⅔, the cuff's pressure which gives amplitude D7 the first amplitude becoming smaller consecutively than either the D1 or Dave, is the diastolic pressure reading 65 mmHg. Since it is also the same as in the auscultatory method, this method is also effective for the non-invasive blood pressure measurement.

Figure 4:
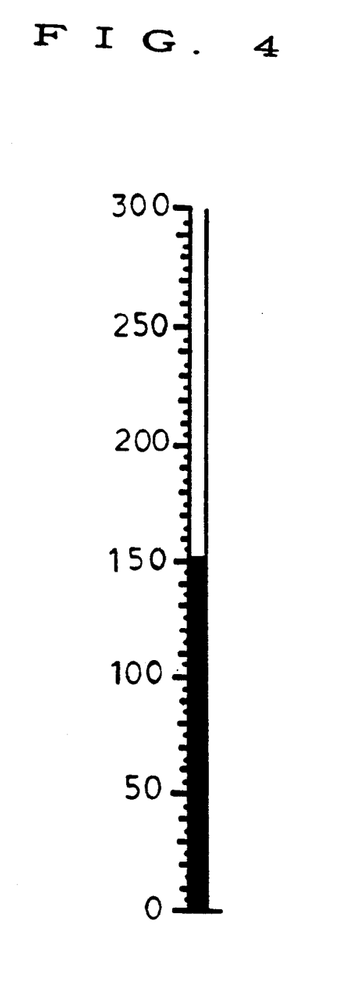
FIG. 4 is a display of a simulated mercury manometer.
Figure 5:
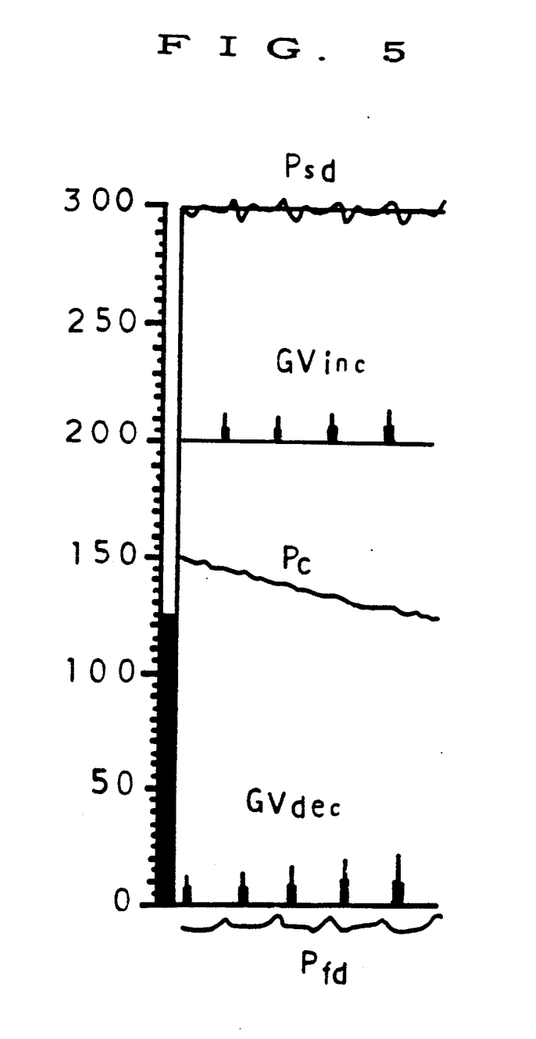
FIG. 5 is a display of the arterial response about five seconds after starting the blood pressure measurement.

A fifth example is to be explained. This example is the blood pressure measuring method with the apparatus laid out in FIG. 1. The method bases on the acquired arterial response process being displayed in real time on the display unit 7. Following the non-invasive apparatus as shown in FIG. 1, cuff 1 being wrapped around a finger or an arm or a leg is to be inflated with a pressurizing unit 3 comprising a small pump or the like, in order to press artery 4. The cuff pressure is then detected with transducer 5 and its pressure readings are displayed on the display unit 7 through the data processing unit 6. On a display unit 7, the pressure reading which was converted to a height information of mercury manometer at unit 6 is displayed in real time as if it were the mercury column of sphygmomanometers as shown in FIG. 4.

While watching in real time the pressure reading (the height) displayed on the mercury manometer, the cuff pressure on the subject's artery is raised a little above subject's systolic pressure reading. When the cuff's pressure starts bleeding, the time and pressure scales are displayed along the X and Y axis respectively. Setting the time axis at arbitrary position, there are simultaneously displayed on unit 7 in real time the trend of the cuff's pressure Pc, the acceleration of the arterial wall's displacement $P_{sd}$, and the increased and decreased amount of the velocity component, GVinc and GVdec as those in the first example, or the time trend of GAinc, GAdec and $P_{fd}$.

Then, there are also displayed Dmax as shown in FIGS. 2 and 3, threshold Dmax-⅔ in FIG. 2 being calculated with Dmax, and either of D1 and Dave in the fourth example as shown in FIG. 3. Thus it becomes possible to measure the blood pressure non-invasively while monitoring the artery response to the pulsating blood flow in real time. Further it can store the response process at the memory unit 9. It also can transmit the acquired data from the data communication unit 10 to other instruments capable of simultaneously measuring or inversely receiving the data from them through a communication network, a telemeter and the likes.

Therefore, according to this non-invasive measurement, the arterial response characterized by the wall motion can be monitored in real time. Thus, transmitting the monitored data to other instruments becomes possible. Reversibly, it becomes possible first to receive the data from the other instruments capable of simultaneously monitoring the same object, for example a brain wave monitor and the likes, and then to display it as an analog quantity in real time. As this result, the non-invasive blood pressure measurement can be effectively made.

I claim:
1. A method of measuring blood pressure using a cuff, pressurizing unit and bleeding valve, comprising:
   squeezing an artery by pressurizing the cuff, the artery having a stretchable wall;
   deflating the cuff;
   indicating the cuff pressure;
   determining changes in displacement velocity of the arterial wall's displacement as the wall stretches and contracts in response to a pulsating blood flow through the artery; and
   comparing the changes in displacement velocity to determine blood pressure as indicated by the cuff pressure.

2. The method of claim 1 wherein determining the changes in displacement velocity of the arterial wall's displacement comprises:
   acquiring the acceleration component of the arterial wall's displacement; and
   from the acceleration component, determining the increased and decreased changes in displacement velocity as the wall stretches and contracts.

3. The method of claim 2 wherein acquiring the acceleration component of the arterial wall's displacement comprises:
   acquiring the arterial wall's displacement with a displacement transducer; and
   determining the acceleration component from the wall's displacement over time.

4. The method of claim 2 wherein acquiring the acceleration component of the arterial wall's displacement comprises:
   acquiring the velocity of the arterial wall's displacement with a displacement velocity transducer; and
   determining the acceleration component from the wall's displacement velocity.

5. The method of claim 1 wherein comparing the changes in displacement velocity to determine blood pressure comprises:
   detecting a maximum decreased displacement velocity change;
   establishing a threshold level of decreased velocity change at a predetermined fraction of the maximum detected change; and
   detecting consecutive decreased velocity changes that exceed the threshold level to determine systolic pressure.

6. The method of claim 1 wherein comparing the changes in displacement velocity to determine blood pressure comprises:
   detecting a maximum decreased displacement velocity change;
   establishing a threshold level of decreased velocity change at a predetermined fraction of the maximum detected change; and
   detecting consecutive decreased velocity changes that are less than the threshold level to determine diastolic pressure.

7. The method of claim 1 wherein comparing the changes in displacement velocity to determine blood pressure comprises:

determining a decreased displacement velocity change corresponding to systolic pressure;

determining first and second decreased velocity changes occurring, respectively, immediately before and immediately after the velocity change corresponding to systolic pressure;

averaging the three velocity changes to obtain an average velocity change; and detecting a decreased displacement velocity change that is less than either the first velocity change or the average velocity change to determine diastolic pressure.

8. The method of claim 1 wherein comparing the changes in displacement velocity to determine blood pressure comprises:

detecting large (Lm) and small (Sm) increased changes in displacement velocity that accompany each pulsation of the blood flow through the artery, where $m = 0, 1, 2, \ldots$;

determining an amplitude difference $\Delta Am$ between Lm and Sm for each pulsation; and detecting an increase in the amplitude difference $\Delta Am$ between consecutive pulsations to determine systolic pressure.

9. The method of claim 1 wherein comparing the changes in velocity to determine blood pressure comprises:

detecting large (Lm) and small (Sm) increased changes in displacement velocity that accompany each pulsation of the blood flow through the artery, where $m = 0, 1, 2, \ldots$;

determining a time difference $\Delta Tm$ between Lm and Sm for each pulsation; and detecting an increase in the time difference $\Delta Tm$ between consecutive pulsations to determine systolic pressure.

10. A blood pressure measuring apparatus comprising:

a cuff having tubes therein for wrapping around and applying pressure to an artery;

a pressurizing unit to inflate the cuff;

a bleeding valve to deflate the cuff;

a pressure transducer to detect fluctuating pressure within the cuff;

a displacement transducer to detect displacement of the arterial wall;

a velocity transducer to detect the velocity of the wall displacement;

data processing means coupled to the transducers for determining the acceleration component of the arterial wall's displacement and, from the acceleration, determining changes in displacement velocity over time; and control means for controlling the pressurizing unit, bleeding valve and data processing means.

11. The apparatus of claim 10 including a display unit operably coupled to the data processing means for displaying the instantaneous fluctuating pressure of the cuff as the height of a mercury column in a scaled manometer glass tube.

12. The apparatus of claim 10 including a display unit operably coupled to the data processing means for displaying over a time scale the instantaneous fluctuating pressure of the cuff, the acceleration component of the arterial wall's displacement, the increased and decreased displacement velocity changes, and the instantaneous velocity component of the arterial wall's displacement.

13. The apparatus of claim 10 including a display unit operably coupled to the data processing means for displaying over a time scale a threshold level of decreased displacement velocity change for comparison with a plurality of decreased velocity changes to visually determine systolic and diastolic pressure.

14. The apparatus of claim 10 including a data communication unit for continuously transmitting or receiving instantaneous fluctuating cuff pressure, acceleration and velocity data from or to other instruments.

15. A method of measuring dynamic parameters of arterial wall motion against decreasing pressure of a pressurized cuff, comprising;

squeezing an artery by pressurizing the cuff, the artery having a stretchable wall that is displaced in response to a pulsating blood flow through the artery;

deflating the cuff to decrease the cuff pressure;

determining acceleration of the arterial wall's displacement as the wall stretches and contracts; and from the acceleration, determining changes in velocity of the arterial wall's displacement over time.

16. The method of claim 15 wherein determining acceleration of the arterial wall's displacement comprises:

acquiring the arterial wall's displacement with a displacement or pressure transducer coupled to the cuff; and taking the second derivative of the displacement or cuff pressure to determine the acceleration.

17. The method of claim 15 wherein determining acceleration of the arterial wall's displacement comprises:

acquiring the instantaneous velocity of the arterial wall's displacement with a velocity transducer; and taking the first derivative of the instantaneous velocity to determine the acceleration.

18. The method of claim 15 including:

determining the instantaneous velocity of the arterial wall's displacement; and displaying on a display unit the acceleration and instantaneous velocity as a function of time.

19. The method of claim 15 including displaying on the display unit the changes in displacement velocity separately as increased changes as a function of time and decreased changes as a function of time.

20. The method of claim 15 including:

indicating the cuff pressure; and measuring blood pressure as indicative by the cuff pressure from the changes in velocity of the arterial wall's displacement.

* * * * *

UNITED STATES PATENT AND TRADEMARK OFFICE
CERTIFICATE OF CORRECTION

PATENT NO. : 5,222,020

DATED : June 22, 1993

INVENTOR(S) : Fumihide Takeda

It is certified that error appears in the above-identified patent and that said Letters Patent is hereby corrected as shown below:

Col. 12, line 58, "indicative by the" should be --indicated by the--.

Signed and Sealed this

Twenty-sixth Day of April, 1994

Attest:

BRUCE LEHMAN

Attesting Officer

Commissioner of Patents and Trademarks